United States Patent [19]

Ullman et al.

[11] 3,996,345

[45] Dec. 7, 1976

[54] FLUORESCENCE QUENCHING WITH IMMUNOLOGICAL PAIRS IN IMMUNOASSAYS

[75] Inventors: Edwin F. Ullman, Atherton; Moshe Schwarzberg, Palo Alto, both of Calif.

[73] Assignee: Syva Company, Palo Alto, Calif.

[22] Filed: June 30, 1975

[21] Appl. No.: 591,386

Related U.S. Application Data

[63] Continuation-in-part of Ser. No. 497,167, Aug. 12, 1974, abandoned.

[52] U.S. Cl. .............................. 424/12; 23/230 B; 195/103.5 R; 260/112 B; 252/301.16
[51] Int. Cl.$^2$ .................. G01N 21/00; G01N 33/16
[58] Field of Search ..................... 23/230 B; 424/12; 195/103.5 R; 260/112 B; 252/301.16

[56] References Cited

UNITED STATES PATENTS

| | | | |
|---|---|---|---|
| 3,901,654 | 8/1975 | Gross | 23/230 B |
| 3,935,074 | 1/1976 | Rubenstein | 23/230 R X |

*Primary Examiner*—Morris O. Wolk
*Assistant Examiner*—Sidney Marantz
*Attorney, Agent, or Firm*—Townsend and Townsend

[57] ABSTRACT

Immunoassays employing antibodies and a fluorescer-quencher (F–Q) chromophoric pair, wherein one or both of the chromophoric pair are bonded to antibodies. Depending on the particular ligand of interest, various reagent combinations can be employed, where the amount of quenching is directly related to the amount of ligand present in the assay medium. In carrying out the assay, the unknown and antibody specific for the ligand of interest to which is bound one of the F–Q pair, are combined in an aqueous buffered medium. Depending on the protocol, different assay reagents are employed in the aqueous buffered medium: (1) ligand analog bonded to the other of the F–Q pair; (2) antibodies specific for the ligand to which is bound the other of the F–Q pair or; finally, (3) a combination of a plurality of ligands bonded together through linking groups to a hub molecule, usually a polymer, in combination with antibody bound to the other of the F–Q pair. The composition is irradiated with light at a wavelength, absorbed by the fluorescing molecule and the amount of fluorescence determined. By employing appropriate standards, the presence and amount of the ligand can be determined.

38 Claims, No Drawings

FLUORESCENCE QUENCHING WITH IMMUNOLOGICAL PAIRS IN IMMUNOASSAYS

CROSS REFERENCE TO RELATED APPLICATIONS

This application is a continuation-in-part of application Ser. No. 497,167, filed Aug. 12, 1974, now abandoned.

BACKGROUND OF THE INVENTION

1. Field of the Invention

There is a continuing need for rapid sensitive methods for determining minute amounts of organic compounds. A number of techniques have been developed toward this end. Among the commercially available techinques are radioimmunoassay, spin-labeled immunoassay, for which reagents are sold under the trademark FRAT, homogeneous enzyme immunoassay, for which reagents are sold under the trademark EMIT, and hemagglutination (HI). These techniques are effective for determining amounts of materials in the range of $10^{-6}$ to $10^{-10}$M or less.

These techinques all involve the ability of a receptor molecule, usually an antibody, to be able to recognize a specific spatial and polar organization of a molecule. Except for hemagglutination, the techniques depend upon providing a reagent which can compete with the molecule being assayed for the receptor. By being able to distinguish between the reagent which is bound to receptor and reagent which is unbound, one can determine the amount of the compound of interest which is present.

In developing immunoassays, one is limited by the availability and properties of an appropriate receptor. However, as for the other reagents and the techinque of measurement, there are a number of different considerations which made for a more accurate, convenient or commercially desirable assay. First, it is desirable that there be a minimum number of measurements of the various reagents, as well as transfers of the various reagents. Secondly, the equipment for measuring should be reasonably economical, so as to be accessible to a broad range of users. Thirdly, the reagents employed should be relatively stable, so as to be capable of storage and shipment. Fourthly, the method should not be subject to significant interference from other materials which may be adventiously present in the sample to be assayed. Other considerations are ease of training of technicians absence of health hazards, sensitivity, reproducibility, and applicability to a wide variety of ligands.

The subject invention is predicated on the phenomenon of energy transfer between two chromophores. When a fluorescing chromophor is irradiated with light absorbed by the chromophore, the fluorescing chromophore can dissipate the energy of the absorbed light by emitting light of longer wavelength, that is, fluorescing. If another chromophore is within less than 100A of the fluorescer and absorbs light at the wavelength of emission, there is a probability, depending upon other factors, that the fluorescer will transfer to the other chromophore the energy which would otherwise have been emitted as light, in effect, quenching the fluorescer.

DESCRIPTION OF THE PRIOR ART

U.S. Pat. No. 3,709,868 is exemplary of a radioimmunoassay. U.S. Pat. No. 3,690,834 is exemplary of a spin immunoassay. U.S. Pat. Nos. 3,654,090 and 3,817,837 are exemplary of enzyme immunoassays. Articles of interest include an article by Ludwig Brand and James R. Gohlke, entitled, Fluorescence Probes for Structure, Annual Review of Biochemistry, 41, 843–868 (1972); and Stryer, Science, 162, 526 (1968). Also of interest is co-pending application Ser. No. 402,693, filed Oct. 2, 1973.

SUMMARY OF THE INVENTION

A method is provided for determining the presence or amount of an organic compound to which a receptor, usually antibody, is vailable or can be prepared. The organic compound will be hereinafter referred to as a ligand.

In carrying out the assay, two chromophores are employed which are a fluorescer-quencher pair. The amount of fluorescer within quenching distance of quencher is affected by the amount of ligand present in the assay medium.

One chromophore is introduced into the assay medium covalently bonded to a receptor composition which specifically binds to the ligand. The second chromophore can be introduced into the assay medium in different ways: (1) covalently bonded to a receptor composition which is the same or different from the receptor composition conjugated to the first chromophore, but in both instances specifically binds to the ligand, and in the presence or absence of polyligand; or covalently bonded to ligand analog, where the ligand analog can compete with ligand for the receptor composition. The choice of modes of introduction will depend to a significant degree on the number of independent epitopic or haptenic sites present in the ligand.

Where the ligand has only one independent epitopic site (monoepitopic), usually one chromophore will be covalently bonded to a receptor for ligand, and the other chromophore will be provided as covalently bonded to a ligand analog or a combination of poly(ligand analog) and the chromophore covalently bonded to receptor for ligand.

Where the ligand has a plurality of independent epitopic sites (polyepitopic), the modes indicated above may be used in addition to the following modes. In one mode, the two chromophores are individually bonded to receptor for ligand. In another mode, receptor for ligand is obtained from different species and one chromophore is bonded to receptor for the ligand-receptor from one species and the other chromophore bonded to receptor for ligand-receptor from the other species. The latter method expands the versatility of the subject assay in allowing for common reagents for a wide variety of assays, simplifies purification procedures, and allows for the determination of the presence of assemblages, as distinct from the component parts.

The various materials are brought together in an aqueous buffered medium, incubated and irradiated with light absorbed by the fluorescer molecules. By determining the amount of fluorescence, after incubation for a predetermined time interval or after the system has approached equilibrium, and comparing the results obtained with one or more known standards, the presence or amount of ligand can be determined.

DESCRIPTION OF THE SPECIFIC EMBODIMENTS

Definitions

Ligand--an organic molecule or assemblage, normally greater than 100 molecular weight and having at least one functionality, normally polar, for which a receptor is either naturally available or can be prepared.

Ligand analog--a mono- or polyvalent radical a substantial proportion of which has the same spatial and polar organization as the ligand to define one or more determinant or epitopic sites capable of competing with the ligand for the binding sites of a receptor, and differs from the ligand in the absence of an atom or functional group at the site of binding to another molecule or in having a linking group which has been introduced in place of one or more atoms originally present in the ligand. The ligand analog precursor is the compound employed for conjugating ligand or ligand analog to another molecule, e.g. chromophore.

Assemblage--a combination of organic molecules bound together by other than covalent bonds, generally having molecular weight exceeding 600, usually exceeding 1,000 and may be 1,000,000 or more, for which receptor is either naturally available or can be prepared; an illustrative assemblage is an antigen and antibody) or, a molecule prepared from two discrete entities, normally joined together by weak bonds, such as polar bonds or disulfide bonds, which under the conditions of the system are capable of being in equilibrium with the individual entities.

Chromophore--a fluorescer or quencher molecule; in the subject invention, the fluorescer and quencher are interrelated. The fluorescer molecule is a chromophore which is able to absorb light at one wavelength and emit light at a longer wavelength. The quencher molecule is capable of inhibiting fluorescence, when within a short distance, usually less than about 100A, of the fluorescer molecule, by accepting the energy which would otherwise be emitted as fluorescent light. As far as the molecule or composition to which the chromophores are joined, in most instances, the fluorescer and quencher will be interchangeable, although there will frequently be some preference. Therefore, for purposes of generality, the two molecules will be referred to as chromophores, and individually referred to as $Ch_1$ and $Ch_2$.

Ligand analog-chromophore (ligand analog-$(Ch_2)_x$)—ligand analog is covalently bound to one or more fluorescent molecules or quencher molecules. With small ligands, those below about 10,000 molecular weight, usually below about 2,000 molecular weight, the ligand analog will usually be joined to fewer than 10 chromophores, usually from 1 to 10 chromophores, not more than about 1 chromophore per 1,000 molecular weight. With a large ligand, at least 2,000 molecular weight, usually at least about 10,000 molecular weight, a plurality of chromophores may be covalently bound to ligand analog. The number of chromophores present will be limited by the number which may be introduced without masking too many epitopic sites of the ligand and the desire to have a sufficient number of chromophores to insure a substantial amount of quenching when receptor-$Ch_1$ is bound to the ligand analog-$(Ch_2)_x$.

Poly(ligand analog)-poly(chromophore) [poly(ligand analog)-poly($Ch_2$)]—ligand analog and chromophore are bonded to a high molecular weight (as compared to the ligand analog and chromophore) water soluble polyfunctionalized hub or nucleus molecule, to provide a plurality of ligand analog groups and chromophore groups spaced on the surface of the molecule, so that when receptor-$Ch_1$ is bound to ligand analog, some $Ch_1$ groups will be present within quenching distance of $Ch_2$ groups.

Poly(ligand analog)—ligand analog groups are bonded to a high molecular weight (as compared to ligand analog) water soluble polyfunctionalized hub or nucleus molecule, so that there are a sufficient number of ligand analogs per unit area for quenching to occur when the poly(ligand analog) is saturated with receptor-$Ch_1$ and receptor-$Ch_2$ in appropriate proportions.

Receptor-chromophore (receptor-$Ch_1$ and receptor-$Ch_2$)—a receptor is a molecule which is capable of distinguishing an epitopic site and binding to such site. Usually receptors will have binding constants in excess of $10^4$, frequently, in excess of $10^6$. For the most part, receptors are antibodies, although enzymes, nucleic acids, and certain globulins, may also act as receptors. In the subject invention, for the most part, the receptors will be antibodies to which one or more, usually at least two or more, chromophore groups will be bound.

Receptor composition—receptor composition is a homogeneous or heterogeneous composition capable of specific non-covalent binding to ligand and ligand analog and includes a composition which specifically recognizes the ligand(anti-ligand) and a combination of anti-ligand and a composition which specifically recognizes the anti-ligand (anti(anti-ligand)).

General Statement of the Invention

The method is predicated on the employment of two chromophores which form a fluorescer-quencher pair. By having a composition (receptor) which specifically recognizes or binds to a ligand to which one of the chromophores is covalently bonded, and having the second chromophore bonded to ligand analog or receptor, the amount of ligand present in the assay solution will affect the amount of quencher within quenching distance of fluorescer. The assay may be carried out competitively, where ligand analog competes with ligand for receptor, ligand analog being present as poly(ligand analog) or covalently bonded to chromophore. The assay may also be carried out non-competitively with ligands having a plurality of epitopic sites, where receptor having each of the chromophores binds to ligand.

Compositions

Depending upon the particular protocol employed and the ligand of interest, one or more of the following reagent compositions will be employed in the assay medium: ligand analog-chromophore, poly(ligand analog)-poly(chromophore), poly(ligand analog), one or two receptors and one or two receptor-chromophores. The first composition to be considered will be the ligand analog-chromophore.

Ligand Analog-Chromophore and Poly(Ligand Analog)-Poly(Chromophore)

The ligand analog-chromophore may be subdivided into two groups. The first group is where the ligand analog-chromophore has a single ligand analog and a single chromophore joined together by a relatively short linking group. In these instances, the ligand analog for the most part will be haptenic, rather than antigenic, and generally be less than about 10,000 molecular weight, more usually less than about 6,000 molecular weight, and frequently in the range of about 125 to 1,000 molecular weight, excluding the linking group employed for linking to the chromophore. For the most part, the ligand analog will differ from the ligand in having a particular functionality replaced by a bond, a hydrogen replaced by a bond, or a short carbon chain replaced by a bond (by bond, it is intended to include multiple bonds, as well as single bonds) to join to the linking group for linking to the chromophore. The various haptenic or low molecular weight ligands will be discussed subsequently.

The linking group will normally have not more than about 10 atoms in the chain between the ligand and the chromophore, more usually having either a bond or from about 1 to 6 atoms in the chain. The atoms for the most part will be carbon, oxygen, nitrogen and sulfur, particularly carbon, oxygen, and nitrogen.

The functionalities involved in the linking group will normally be non-oxo carbonyl (including imino and thionocarbonyl) oxy, amino (particularly tertiary amino or quaternary) or combinations thereof, e.g. amido, carbamyl, and amidino.

The two chromophores, either fluorescer or quencher, will normally have either an amino or alcohol function for reacting with a non-oxo carbonyl function (including the nitrogen and sulfur analogs thereof) or have a non-oxo carbonyl function, which can be reacted with an amine or alcohol functionality.

Where the ligand is of at least 2,000 molecular weight, a plurality of chromophore groups may be bound to the ligand. Usually, there will be at least one chromophore group per 20,000 molecular weight, more usually at least one chromophore group per 10,000 molecular weight and not more than one chromophore group per 1,000 molecular weight, more usually not more than one chromophore group per 2,000 molecular weight. The considerations concerning the number of chromophores conjugated to the ligand have been previously enumerated. The linking groups will be as previously described. Usually, the ligand will be an antigenic polypeptide or protein having a plurality of amino groups. Active halogen or nonoxo carbonyl (including nitrogen and sulfur analogs) can be used for conjugation to form a covalent bond or amides, amidines, thionoamides, ureas, guanidines and thioureas.

Alternatively, the ligand and chromophore ($Ch_1$ or $Ch_2$) may be linked to a hub molecule (poly(ligand analog)-poly(chromophore). The hub molecule or nucleus molecule can be employed with advantage for a variety of reasons. The nucleus molecule will generally be a polymeric molecule of relatively high molecular weight, normally in excess of 20,000 molecular weight, frequently 60,000 molecular weight, and may be 10 million or higher. The nucleus molecule will normally be water soluble or dispersible in an aqueous medium to provide a stable dispersion, where the dispersible material does not interfere with the absorption or irradiation of light. The nucleus molecule may be a naturally occurring material, a modified naturally occurring material, or synthetic. Included among nucleus molecules are polypeptides, proteins, polysaccharides, synthetic polymers, and the like. The nature of the hub molecule may be widely varied, so long as it is sufficiently functionalized to permit the introduction of the ligand and the chromophore molecules.

Among proteins which can find use are albumins, globulins, proteoglycans, and the like; among polysaccharides are amylose, cellulose, agarose, dextrans, or the like, either as obtained or partially degraded; among synthetic polymers, polyvinylalcohol, acrylates, copolymers thereof or the like may be employed.

Normally, there will be not less than about one conjugate (ligand analog or chromophore) molecule per 50,000 molecular weight, more usually not less than about one conjugate molecule per 25,000 molecular weight, and usually not more than about one conjugate molecule per 1,000 molecular weight, more usually not more than about one conjugate molecule per 2,000 molecular weight.

The ratio of chromphore molecules to ligand will generally be from about 0.05–20:1, more usually from about 0.5–20:1, preferably from about 1–10:1, and more preferably from about 2–8:1.

Where the chromophore is the fluorescer molecule for the purposes of this invention, generally there will be at least about 0.5–20, more usually from about 1–10, and preferably from about 2–7 fluorescing molecules per ligand molecule. Where the chromophore is the quencher molecule, the number of quencher molecules per ligand will generally be from about 0.5–20, more usually from about 1–20, and preferably from about 2–15 per ligand molecule.

The conjugates to the hub molecule will have the same type of linking group as was employed for joining the chromophore to the ligand. The particular choice of functionality will depend upon the available functional groups on the nucleus molecule.

Receptor-Chromophore

Since in most instances the receptor is antibody, the present description will refer to antibody as exemplary of receptor. Antibodies have a number of active amino groups which can be used for covalently conjugating the chromophore to the antibody. Conveniently, the chromophore can have a non-oxo carbonyl functionality (including the nitrogen and sulfur analogs thereof) or active $\alpha$-halocarbonyl functionality. Illustrative functionalities for linking the chromophore to the antibody include acyl halides, mixed anhydrides, imidate alkyl esters, isothiocyanate, chlorobromo- or iodoacetyl, and the like.

The conditions for conjugation employ moderate temperatures 0° to 40° C, in aqueous media at moderate pH. Conjugation of chromophores to protein is known in the art. The, et al., Immunology, 18, 865 (1970); Cebra, et al., J. Immunol., 95, 230 (1965); Goldman, Fluorescent Antibody Methods, Academic Press, New York (1968).

The number of chromophore groups which are conjugated to the antibody may be varied over a relatively broad range, depending on the chromophore involved. There will be at least one chromophore group per antibody, and usually on the average, from about 2 to 30, more usually from about 3 to 25 chromophore groups per antibody. Where the chromophore is the fluorescer, the average number of chromophore groups per antibody will be from about 1 to 20, usually 2 to 15 and more usually 2 to 10. Where the chromophore is the quencher, the average number of chromophore groups per antibody will be from about 2 to 30, usually 3 to 25, and more usually 5 to 25.

It should also be noted that when antibodies are prepared for a ligand having a plurality of epitopic sites, the receptor composition is not homogeneous. That is, the receptor will have antibodies which recognize different epitopic sites. In referring to receptor, it is intended to include all the antibodies which are capable of specifically binding to any of the epitopic sites of the ligand.

Poly(Ligand Analog)

The poly(ligand analog) differs from the ligand analog-chromophore and poly(ligand analog)-poly(chromophore) in that no chromophore is present, only ligand analog. The same types of nucleus molecules and the same degree of conjugation apply for the poly(ligand analog) as for the poly(ligand analog)-poly(chromophore). However, the ligand analog may be present in much higher ratio than the hub nucleus can accomodate receptor. Therefore, while a minimum number of ligand analog groups are essential, the maximum number is one of expedience. The significant factor is that receptor molecules when bound to poly(ligand analog) can come sufficiently close to allow the chromophores to come within quenching distance.

In choosing a nucleus molecule, a number of considerations will bear on the choice. While it is not essential that the nucleus molecule be water soluble, in most instances, it will be desirable. In any event, the nucleus molecule or composition will be capable of stable dispersion in an aqueous medium. Secondly, the nucleus molecule should not absorb light at the emission wavelength of the fluorescer to cause significant quenching. Thirdly, the nucleus molecule should not fluoresce at the emission wavelengths of the fluorescer when irradiated with the exciting light. Therefore, any significant absorption by the nucleus molecule should be below about 520nm, preferably below about 450nm.

The nucleus molecule should be highly functionalized, preferably with amino or hydroxyl groups, although other reactive functionalities are also useful, e.g. carboxy. Fourthly, the nucleus molecule should be stable under conditions of storage and use. Fifthly, the nucleus molecule should be inert to functionalities present in the chromophore and ligand, other than the functionality for linking. Finally, the nucleus molecule should not interfere with the immunoassay, for example, by having naturally occurring receptors which may be present in physiological fluids which are studied.

While any size of molecule may be employed, very large molecules or cells will create practical problems. For example, a very large molecule passing through the light beam of the fluorometer could provide a sudden increase in the peak height. Therefore, the signal obtained would have to be averaged over a reasonable period of time. Large molecules will also result in increased scatter, but the scatter could be compensated for by an appropriate optical system. Preferably, for the most part, molecules will be employed which are less than about 10 million molecular weight, more preferably from about 30,000 to 1,000,000 molecular weight.

Chromophore

Since antibodies are normally present in the assay medium, and proteins absorb light of wavelengths up to about 310nm, the fluorescer will have substantial absorption higher than 310nm, normally higher than 350nm, and preferably higher than about 400nm. The choice of fluorescer will also be governed by the particular ligand of interest. The fluorescer should absorb light at a higher wavelength than the ligand or ligand analog of interest. A high extinction co-efficient is desirable, greatly in excess of 10, preferably in excess of $10^3$, and particularly preferred in excess of $10^4$. A good quantum yield should be available in the aqueous medium for the fluorescer. As a matter of convenience, the absorption peak of the fluorescer should not vary significantly with variation in the ligand.

A number of different fluorescers are described in the articles previously noted; namely, Stryer, supra, and Brand, et al., supra.

One group of fluorescers having a number of the desirable properties described previously are the xanthene dyes, which include the fluoresceins derived from 3,6-dihydroxy-9-phenyl-xanthhydrol and rosamines and rhodamines, derived from 3,6-diamino-9-phenylxanthhydrol. The rhodamines and fluoresceins have a 9-o-carboxyphenyl group, and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate.

Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, such as 4-chloro-7-nitrobenzo-2-oxa-1,3-diazole and 7-(p-methoxybenzylamino)-4-nitrobenzo-2-oxa-1,3-diazole; stilbenes, such as 4-dimethylamino-4'-isothiocyanatostilbene and 4-dimethylamino-4'-maleimidostilbene; N,N'-dioctadecyloxacarbocyanine p-toluenesulfonate; pyrenes, such as 8-hydroxy-1,3,6-pyrenetrisulfonic acid, and 1-pyrenebutyric acid, merocyanine 540, rose bengal, 2,4-diphenyl-3(2H)-furanone, as well as other readily available fluorescing molecules. These dyes, either have active functionalities or such functionalities may be readily introduced.

Similar considerations involved with the fluorescer molecule are applicable to the quenching molecule, except that a good fluorescent quantum yield is not required where fluorescence of the fluorescer is being measured. An additional consideration for the quenching molecule is that it has its absorption at an emission wavelength of the fluorescer. Good overlap of the fluorescer emission and quencher absorption is desirable.

It should be noted that both the absorption and emission characteristics of the dye may vary from being free in solution and being bound to a protein or ligand. Therefore, when referring to the various ranges and characteristics of the dyes, it is intended to indicate the dye as employed and not the dye which is unconjugated and characterized in an arbitrary solvent. In the area of overlap between fluorescence and quenching, the quencher should have extinction coefficients of the same order or higher than those set forth for absorption by the fluorscing molecule.

Ligand

As indicated, the ligand will vary widely, normally having a molecular weight of at least 110, more usually at least 125 with the maximum molecular weight unlimited, although usually not exceeding 10 million. For the most part, the significant factor concerning a ligand is that a receptor can be made to the ligand or is available. Normally, receptors can be made for most organic compounds having a polar functionality. Compounds for which antibodies can be formed by bonding the compound to a compound having antigenic properties are referred to as haptens. Those compounds which elicit antibody formation without chemical modification are referred to as antigens. See Kabat, et al., Experimental Immunochemistry, Charles C. Thomas, Springfield, Illinois, 1967.

The non-polymeric ligands of interest will normally be of from about 125 to 2,000 molecular weight. These compounds involve a wide variety of compounds of varying structure, functionality, and physiological properties. The compounds may be acyclic, alicyclic or heterocyclic, both mono- and polycyclic. The heteroatoms involved include oxygen, nitrogen, sulfur, halogen (fluorine, chlorine, bromine and iodine) boron, phosphorous, metal cations of Groups 1A and 2A of the Periodic Chart, transition metals, and the like.

The functionalities include alcohols, ethers, carboxylic acids, esters and amides, amines (primary, secondary, tertiary and quaternary) halo, nitrilo, mercapto, and the like. Normally, the compounds will be composed solely of carbon, hydrogen, oxygen, nitrogen, halogen and phosphorous, particularly carbon, hydrogen, oxygen, and nitrogen and where salts are involved, the appropriate metal counterion or ammonium counterion.

Heterocyclic rings which are present include pyrrole, pyridine, piperidine, indole, thiazole, piperazine, pyran, coumarin, pyrimidine, purine, triazine, imidazole, and the like.

Because of the wide variety of compounds which can be determined in accordance with the subject assay, the different groups will be broken down into various, frequently artificial, categories, either by the presence of a particular functionality or ring structure, or because of sharing a particular function or because of being recognized as a class.

The first class of compounds of interest are those having an amino group, either as a heterocyclic member, or as a functionality on an aliphatic chain. These compounds will normally be of from about 110 to 800 molecular weight, more usually of about 125 to 650 molecular weight. These compounds frequently have an amino group separated by 2 to 3 aliphatic carbon atoms from a benzene ring.

The first group of compounds of interest are the alkaloids and the metabolites of those alkaloids which are ingested. The first group of important alkaloids are alkaloids of the morphine group. Included in this group are morphine, codeine, heroin, morphine glucuronide and the like.

The next group of alkaloids are the cocaine alkaloids, which includes, particularly as metabolites, benzoyl ecgonine and ecgonine.

Another group of alkaloids are the cinchona alkaloids which includes quinine.

The isoquinoline group of alkaloids includes mescaline.

The benzylisoquinoline alkaloid group includes papaverine.

The phthalide isoquinoline alkaloid group includes narcotine, narceine, and cotarnine.

The indolopyridocoline alkaloid group includes yohimbine and reserpine.

The ergot alkaloid group includes ergotamine and lysergic acid.

Other groups of alkaloids are strychnine alkaloids, pyridine alkaloids, piperidine alkaloids, pyrrolizidine alkaloids, and the like.

The alkaloids of primary interest are those which come within the category of drugs of abuse, such as morphine, cocaine, mescaline, and lysergic acid, which may be analyzed for the compound or its metabolite, depending on the physiological fluid which is analyzed for its presence.

A number of synthetic drugs mimic the physiological properties, in part or in whole, of the naturally occurring drugs of abuse. Included among these drugs are methadone, meperidine, amphetamine, methamphetamine, glutethimide, diphenylhydantoin, and drugs which come within the category of benzdiazocycloheptanes, phenothiazines and barbiturates.

Drugs of interest because of their physiological properties are those which are referred to as catecholamines. Among the catecholamines are epinephrine, ephedrine, L-dopa, and norepinephrine.

Other drugs of interest are the tranquilizer Meprobamate, Tergitol and succinimides, such as Ethoxsumide.

Other compounds of interest are tetrahydrocannabinol, cannabinol, and derivatives thereof, primarily compounds derived from marijuana, synthetic modifications and metabolites thereof.

Another group of compounds of significant interest are the steroids. The steroids include estrogens, gestogens, androgens, adrenocortical hormones, bile acids, cardiotonic glycoids, algycones, saponins and sapogenins.

Another class of compounds are the vitamins, such as vitamin A, the B group, e.g. vitamin $B_1$, $B_6$, and $B_{12}$, E, K, and the like.

Another class of compounds are the sugars, both the mono- and polysaccharides, particularly di- and higher order polysaccharides.

Another class of compounds is the prostaglandins.

Another class of compounds are the amino acids, polypeptides and proteins. Polypeptides usually encompass from about 2 to 100 amino acid units (usually less than about 12,000 molecular weight). Larger polypeptides are arbitrarily called proteins and are usually composed of from about 1 to 20 polypeptide chains. Poly(amino acid) will be used as generic to polypeptides and proteins. Of particular interest among amino acids is thyronines, both the tri- and tetraiodo. The poly(amino acid)s employed in this invention employing two antibodies as reagents will generally range from about 5,000 to $10^7$, usually $10^4$ to $10^6$ molecular weight. Of particular interest among polypeptides and proteins [poly(amino acids)] are hormones, globulins, antigens and compositions found to have specific physiological activities.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
unclassified proteins, e.g. somalotropin, prolactin, insulin, pepsin A number of proteins found in the human plasma are important clinically and includes:

Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
$\alpha_1$-glycoprotein
$\alpha_1\chi$-Glycoprotein
Thyroxin-binding globulin
Inter-$\alpha$-trypsin-inhibitor
Gc-globulin
 (Gc 1-1)
 (Gc 2-1)
 (Gc 2-2)
Haptoglobin
 (Hp 1-1)
 (Hp 2-1)
 (Hp 2-2)
Ceruloplasmin
Cholinesterase
$\alpha_2$-Lipoprotein(s)
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G (IgG) or $\gamma$G-globulin
Mol. formula: $\gamma_2\kappa_2$ or $\gamma_2\lambda_2$
Immunoglobulin A (IgA) or $\gamma$A-globulin
Mol. formula: $(\alpha_2\kappa_2)^n$ or $(\alpha_2\lambda_2)^n$
Immunoglobulin M (IgM) or $\gamma$M-globulin
Mol. formula: $(\mu_2\kappa_2)^5$ or $(\mu_2\lambda_2)^5$
Immunoglobulin D(IgD) or $\gamma$D-Globulin ($\gamma$D)
Mol. formula: $(\delta_2\kappa_2)$ or $(\delta_2\lambda_2)$
Immunoglobulin E (IgE) or $\gamma$E-Globulin ($\gamma$E)
Mol. formula: $(\epsilon_2\kappa_2)$ or $(\epsilon_2\lambda_2)$
Free light chains
Complement factors:
C'1
 C'1q
 C'1r
 C'1s
C'2
C'3
 $\beta_1$A
 $\alpha_2$D
C'4
C'5
C'6
C'7
C'8
C'9
Important blood clotting factors include:

TABLE VII

| BLOCK CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:
Peptide and Protein Hormones
 Parathyroid hormone (parathormone)
 Thyrocalcitonin
 Insulin
 Glucagon
 Relaxin
 Erythropoietin
 Melanotropin (melanocyte-stimulating hormone; intermedin)
 Somatotropin (growth hormone)
 Corticotropin (adrenocorticotropic hormone)
 Thyrotropin
 Follicle-stimulating hormone
 Luteinizing hormone (interstitial cell-stimulating hormone)
 Luteomammotropic hormone (luteotropin, prolactin)
 Gonadotropin (chorionic gonadotropin)
Tissue Hormones
 Secretin
 Gastrin
 Angiotensin I and II
 Bradykinin
 Human placental lactogen
Peptide Hormones from the Neurohypophysis
 Oxytocin
 Vasopressin
 Releasing factors (RF) CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrhoeae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |

| Species of Microorganisms | Hemosensitin Found in |
|---|---|
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Samonella pullorum | Polysaccharide |
| Shigella dysenteriae | Polysaccharide |
| Shigella flexneri Shigella sonnei | Crude, polysaccharide |
| Rickettsiae | Crude extract |
| Candida albicans | Polysaccharide |
| Entamoeba histolytica | Crude extract |

Another group of compounds are the antibiotics such as penicillin, actinomycin, chloromycetin, and the like.

Individual compounds of interest are serotonin, spermine, and phenylpyruvic acid.

Finally, compounds which are pesticides, such as fungicides, insecticides, bactericides, and nematocides, may also be of interest for assaying.

Other than compounds of interest, cells, viruses, and other biological aggregations which are antigenic or to which naturally occurring receptors can be found may also be assayed for.

The microorganisms which are assayed may be intact, lysed, ground or otherwise fragmented, and the resulting composition or portion, e.g. by extraction, assayed. Microorganisms of interest include:

Cornynebacteria
Corynebacterium diptheriae

Pneumococci
Diplococcus pneumoniae

Streptococci
Streptococcus pyogenes
Streptococcus salivarus

Staphylococci
Staphylococcus aureus
Staphylococcus albus

Neisseriae
Neisseria meningitidis
Neisseria gonorrheae

Enterobacteriaciae
Escherichia coli
Aerobacter aerogenes ⎫
Klebsiella pneumoniae ⎬ The coliform bacteria
Salmonella typhosa ⎭
Salmonella choleraesuis ⎫
Salmonella typhimurium ⎬ The Salmonellae
Shigella dysenteriae ⎭
Shigella schmitzii
Shigella arabinotarda
Shigella flexneri ⎬ The Shigellae
Shigella boydii
Shigella Sonnei Other enteric bacilli
Proteus vulgaris
Proteus mirabilis
Proteus morgani ⎬ Proteus species
Pseudomonas aeruginosa
Alcaligenes faecalis
Vibrio cholerae Hemophilus-Bordetella group
Hemophilus influenzae,
    H. ducreyi
    H. hemophilus
    H. aegypticus
    H. paraiufluenzae Bordetella pertussis Pasteurellae
Pasteurella pestis
Pasteurella tulareusis Brucellae
Brucella melitensis
Brucella abortus
Brucella suis Aerobic Spore-forming Bacilli
Bacillus anthracis
Bacillus subtilis
Bacillus megaterium
Bacillus cereus -continued Anaerobic Spore-forming Bacilli
Clostridium botulinum
Clostridium tetani
Clostridium perfringens
Clostridium novyi
Clostridium septicum
Clostridium histolyticum
Clostridium tertium
Clostridium bifermentans
Clostridium sporogenes Mycobacteria
Mycobacterium tuberculosis hominis
Mycobacterium bovis
Mycobacterium avium
Mycobacterium leprae
Mycobacterium paratuberculosis Actinomycetes (fungus-like bacteria)
Actinomyces israelii
Actinomyces bovis
Actinomyces naeslundii
Nocardia asteroides
Nocardia brasiliensis The Spirochetes
Treponema pallidum
Treponema pertenue
Treponema carateum
Borrelia recurrentis
Leptospira icterohemorrhagiae
Leptospira canicola
Spirillum minus
Streptobacillus moniliformis Mycoplasmas
Mycoplasma pneumoniae Other pathogens
Listeria monocytogenes
Erysipelothrix rhusiopathiae
Streptobacillus moniliformis
Donvania granulomatis
Bartonella bacilliformis Rickettsiae (bacteria-like parasites)
Rickettsia prowazekii
Rickettsia mooseri
Rickettsia rickettsii
Rickettsia conori
Rickettsia australis
Rickettsia sibiricus
Rickettsia akari
Rickettsia tsutsugamushi
Rickettsia burnetii
Rickettsia quintana Chlamydia (unclassifiable parasites bacterial/viral)
Chlamydia agents (naming uncertain)

Fungi
Cryptococcus neoformans
Blastomyces dermatidis
Histoplasma capsulatum
Coccidioides immitis
Paracoccidioides brasiliensis
Candida albicans
Aspergillus fumigatus
Mucor corymbifer (Absidia corymbifera)
Rhizopus oryzae
Rhizopus arrhizus } Phycomycetes
Rhizopus nigricans
Sporotrichum schenkii
Fonsecaea pedrosoi
Fonsecaea compacta
Fonsecaea dermatitidis
Cladosporium carrionii
Phialophora verrucosa
Aspergillus nidulans
Madurella mycetomi
Madurella grisea
Allescheria boydii
Phialosphora jeanselmei
Microsporum gypseum
Trichophyton mentagrophytes
Keratinomyces ajelloi
Microsporum canis
Trichophyton rubrum
Microsporum andouini Viruses -continued Adenoviruses Herpes Viruses
Herpes simplex
Varicella (Chicken pox)
Herpes Zoster (Shingles)
Virus B
Cytomegalovirus Pox Viruses
Variola (smallpox)
Vaccinia
Poxvirus bovis
Paravaccinia
Molluscum contagiosum Picornaviruses
Poliovirus
Coxsackievirus
Echoviruses
Rhinoviruses Myxoviruses
Influenza (A, B, and C)
Parainfluenza (1–4)
Mumps Virus
Newcastle Disease Virus
Measles Virus
Rinderpest Virus
Canine Distemper Virus
Respiratory Syncytial Virus
Rubella Virus Arboviruses
Eastern Equine Eucephalitis Virus
Western Equine Eucephalitis Virus
Sindbis Virus
Chikungunya Virus
Semliki Forest Virus
Mayora Virus
St. Louis Encephalitis Virus
California Encephalitis Virus
Colorado Tick Fever Virus
Yellow Fever Virus
Dengue Virus Reoviruses
Reovirus Types 1–3

Hepatitus
Hepatitis A Virus
Hepatitis B Virus

Tumor Viruses
Rauscher Leukemia Virus
Gross Virus
Maloney Leukemia Virus
Friend Leukemia Virus
Mouse Mammary Tumor Virus
Avian Leucosis Virus
Rous Sarcoma Virus
Polyoma Virus
Simian Virus 40
Papilloma Virus
Preparations of microorganisms include:
Streptococcus pyogenes, protein
Pasteurella pestis, protein toxin
Clostridium tetani, toxoid
Clostridium perfringens, α-lecithinase
Escherichia coli, filtrates
Treponema reiteri, protein extract
Corynebacterium diphtheriae, toxin, toxoid
Mycobacterium tuberculosis, protein
M. tuberculosis, cytoplasm
M. tuberculosis, culture filtrate and tuberculin
Mycoplasma pneumoniae, "crude" antigen Immunoassay The subject immunoassays are based on the degree of quenching occurring in a solution where fluorescent molecules are irradiated with light absorbed by the fluorescer, preferably within the absorption peak, as a function of the amount of ligand in the medium. Thus, the number of fluorescer and quencher molecules which are brought together to within a distance where quenching can occur is related to the amount of ligand present in the assay medium.

The assay can be carried out with receptors for the ligand (anti-ligand) conjugated to the chromophore (anti-ligand)-chromophore or receptor for the anti-ligand (anti-(anti-ligand)) conjugated to the chromophore (anti(anti-ligand)-chromophore). For reasons which will be discussed subsequently, the latter technique (the double receptor technique) provides procedural advantages, as well as providing assay capabilities not available with the single receptor technique. The double receptor technique binds receptor-chromophore indirectly to the ligand through a receptor (antiligand) intermediary, which now allows for an additional degree of freedom in varying the reagents.

In carrying out the assay employing the single receptor technique, the ligand analog reagent has ligand analog bound either directly (covalently) to a chromophore, ligand analog-$(Ch_2)_x$ or poly(ligand analog)-poly($Ch_2$), or indirectly (through receptor-$Ch_2$) to a chromophore ($Ch_2$). The assay is then carried out by combining in the assay medium, the ligand bound to $Ch_2$, receptor-$Ch_1$, and the unknown. Various orders of addition are permissible. Where ligand analog is to be bound indirectly to $Ch_2$, receptor-$Ch_1$ and receptor-$Ch_2$, may be added stepwise or substantially simultaneously.

Conveniently, the receptor-$Ch_1$ and receptor-$Ch_2$ may be combined together as a single reagent at the proper ratio. In this manner, the ratio of the two common receptors can be carefully controlled and accurately added to the assay mixture. The mixture can be a dry lyophilized mixture or an aqueous, normally buffered (pH 5–10; usually 6.5–8.5) solution of any desired concentration.

The concentration of ligand of interest will generally range from about $10^{-4}$ to $10^{-14}$, more usually from about $10^{-6}$ to $10^{-12}$M, most usually $10^{-6}$ to $10^{-10}$M. The concentrations of reagents will reflect the concentration of interest of the ligand.

The medium will normally be aqueous, having from 0 to 40, more usually from 0 to 20 volume percent of a polar organic solvent. Illustrative polar organic solvents include ethylene glycol, ethanol, carbitol, dimethylformamide, dimethylsulfoxide and the like. Preferably, the aqueous medium will be substantially free of other polar solvents. The medium will normally be buffered in the range of about 5 to 10, preferably from about 6.5 to 8.5, and more preferred from about 7 to 8.5. Various buffers may be used, such as borate, phosphate, carbonate, barbituric acid, tris, and the like. The particular buffer employed is not critical to this invention, but in particular assays, one buffer may be preferred over another. The buffer concentration will normally range from about 0.005M to 0.5M, more usually from about 0.01M to about 0.1M.

During the assay, moderate temperatures normally will be employed, generally ranging from about 0° C to 45° C, more usually ranging from about 15° C to 40° C. The particular temperature chosen will depend on convenience, and on the effect of temperature on fluorescence efficiency, and on the binding constant of the receptor to the ligand. The assay performance will be improved at lower temperatures, since both fluorescence efficiency and binding constants are enhanced.

For convenience, the single receptor assays will be divided into those where ligand is bound covalently to chromophore and those where ligand is bound indirectly through receptor to chromophore.

The first assay to be considered will be with those compositions where chromophore is covalently bound to ligand. As previously indicated, a single chromophore may be bound to a single ligand or by employing a nucleus molecule, a plurality of ligands may be bound to a plurality of chromophore groups. Alternatively, with large ligands such as proteins, a plurality of chromophore groups may be bound to the ligand.

The ligand analog-chromophore will generally be at a concentration not greater than 100 times the highest concentration and not less than 0.01 times the lowest concentration of the concentration range of interest, more usually being in the range from the highest concentration of interest to not less than 0.1 times the lowest concentration of interest, and preferably within an order of magnitude or a factor of 10 of the lowest concentration of interest. The receptor-chromophore concentration is then determined by adding a sufficient amount of the receptor to obtain at least 10 percent quenching, preferably at least 20 percent quenching, and up to 100 percent quenching, usually from about 20 to 80 percent quenching, and preferably from about 50 to 80 percent quenching. The amount of receptor-chromophore employed will be related to the binding constant, the concentration of interest which affects the concentration of the ligand-chromophore, the sensitivity of the instrument, and the like.

While the chromophore bound to the ligand may be quencher, for the most part, the chromophore bound to ligand will be fluorescer. This is not a matter of operability, but rather expedience. In most cases, the receptor is antibody, which will be a complex protein mixture, containing antibody for the ligand, as well as other antibodies and proteins. When the antibody composition is labeled with chromophore, a substantial proportion of the chromophore will be bound to protein other than the antibody for the ligand (anti-ligand). Therefore, if fluorescer was bound to receptor, this would result in a large background fluoresence in the assay medium. Alternatively, when a relatively pure sample of anti-ligand is available, the preferred procedure would be to bind ligand to quencher, rather than fluorescer.

The particular order of addition of the various materials to the assay medium is not critical to this invention. The unknown and ligand analog-chromophore may be combined simultaneously with receptor-chromophore or the materials added sequentially. Preferably, the unknown is combined with the receptor-chromophore and incubated for a sufficient time, so as to approach equilibrium. Therefore, the available binding sites of the receptor are reduced in proportion to the amount of unknown present in the assay medium. The ligand analog-chromophore may then be added and incubated and the solution then transferred to a fluorometer and the fluorescence intensity determined on exciting with light at a wavelength or wavelengths absorbed by the fluorescer.

Incubation times will be dependent upon the temperature employed, the binding constant of the receptor and the concentrations of the materials present in the assay medium. Normally, incubation times will be at least about 5 sec and preferably not exceeding about 6 hours, more usually being in the range of about 30 sec to 2 hours, preferably, 1 to 30 min. Temperatures of incubation will generally vary from about 15° to 40° C.

By employing a series of solutions having known concentrations of ligand, one can provide a standard curve relating fluorescence or percent quenching to concentration of ligand. The fluorescence resulting from an assay medium with an unknown can then be directly related to the concentration of the unknown in the assay medium.

In a second mode, in which ligand is bound indirectly to a chromophore, the anti-ligand is divided into two parts and one part conjugated with fluorescer and the other part conjugated with quencher. This mode requires either that the ligand have a plurality of determinant or epitopic sites, or alternatively, that where the ligand has only one or two epitopic sites, a poly(ligand analog) be prepared. That is, the ligand can only accommodate a few, usually from about 1 to 2 antibodies simultaneously. As previously indicated, poly(ligand analog) is prepared by conjugating ligand analog to a nucleus molecule of high molecular weight.

In the assay where the ligand is covalently conjugated to chromophore, the assay response in going from no ligand to increasing concentrations of ligand is a smooth curve with increasing fluorescence, until the maximum amount of fluorescence is obtained. A similar result is observed when one employs poly(ligand analog) to measure ligand and receptor-fluorescer and receptor-quencher. However, with an antigen, which has a plurality of determinant sites and only receptor-quencher and receptor-fluorescer are added to the unknown to be assayed, at zero antigen concentration, there is a maximum fluorescence which diminishes with increasing antigen concentration to reach a minimum and then increases again to maximum fluorescence.

The cause of this biphasic result is straightforward. As antigen is added, quencher and fluorescer are brought together on the surface of the antigen, so that some quenching occurs. With increasing antigen concentration, more and more of the two receptors are brought together at the surface of the antigen with increasing quenching. However, at some concentration, quenching reaches a maximum (fluorescence reaches a minimum). With increasing antigen, the amount of receptor bound to any one antigen diminishes so that the amount of quenching also diminishes. Finally, at high concentrations of antigen, the amount of receptor bound to any one antigen is insufficient to provide quenching. Therefore, when assaying for antigen, it is necessary to carry out the assay at two different dilutions of the antigen. In this way one can determine whether one is on the declining portion or increasing portion of the curve.

The concentration of poly(ligand analog), based on available ligand analog, will fall within the same ranges indicated for the ligand covalently bound to chromophore.

In carrying out the assay with the two conjugated receptors, e.g. antibodies, the antigen is combined with the antibodies usually in the presence of about 0.1 to 1mg/ml of a protein, e.g. albumin, and incubated for a sufficient time, generally from about 5 to 6 hours, more usually from about ½ min to 2 hours, preferably one to 30 min, at a temperature in the range of about 15° to 40° C. The considerations determining the time for incubation have been discussed previously.

With poly(ligand analog), the two conjugated antibodies are combined with the unknown to be assayed, incubated, and the poly(ligand analog) added and the mixture further incubated. The times and temperatures previously indicated are also applicable in this assay.

The sample is then introduced into a fluorometer, and the fluorescence determined upon exciting with light of the appropriate wavelength. The fluorescence may be from the fluorescer or quencher depending upon the wavelength band measured. The assay can be carried out manually or be automated.

The subject method is readily adaptable to determine the presence of antibodies or antigens in human physiological fluid using a two step method and receptor-chromophores ($Ch_1$ and $Ch_2$) for gamma globulin, e.g. human. One can readily differentiate by the difference in molecular weight between the aggregation of antibodies or other receptor molecules which are bound to an antigen and the antibodies or other receptors which are free in solution.

Depending on whether one wishes to determine the presence or absence of an antigen or antibodies in a human physiological fluid, e.g. blood, one would add the complementary material, usually in substantial excess to the maximum concentration of interest. For example, if one wished to determine the presence of antibodies in serum to a particular antigen, one would add the antigen to the physiological fluid and separate components having molecular weights greater than the antibody molecular weight (>160,000), for example, by centrifugation. After separating the precipitate from the supernatant, the precipitate is redispersed and assayed in accordance with the invention for the presence of human gamma globulin. Only in the presence of antigen will human gamma globulin be present in the precipitate. Therefore, the presence of human gamma globulin in the precipitate indicates the presence of antibodies to the antigen in the serum.

The two step method can be used for determining a wide variety of antigens and antibodies using the same receptor-chromophores. The method provides a direct determination of antibodies to specific antigens. Antigens can be indirectly determined by adding antibodies to the fluid suspected of containing the antigen and then assaying for the presence of antibodies in the precipitate after separation of bound and unbound antibodies.

The double receptor technique is a homogeneous technique which allows for the determination of haptens, antigens, and anti-ligand, particularly where the ligand is a polyepitopic antigen.

In the simplest mode, for detection of a ligand, the ligand would be conjugated to a chromophore, particularly fluorescer and anti-ligand and anti(anti-ligand)-chromophore, particularly quencher, added to the assay solution. In this manner, one could bind a larger number of quencher molecules to the ligand, enhancing the opportunity for quenching. In effect, the anti-ligand provides for increasing the number of quencher moleculles capable of being bound to the ligand.

The concentrations of the reagents will parallel the analogous reagents for the single receptor technique with the anti(anti-ligand)-chromophore being in molar excess to the anti-ligand, generally the mole ratio being from about 1.5 to 10:1. If desired, individual $F_{ab}$ units can be employed rather than intact IgG.

The next mode has both chromophores indirectly bound to ligand. In this mode, only anti-ligand and anti(anti-ligand)-$Ch_1$ and anti(anti-ligand)-$Ch_2$ are employed. However, prior to introduction of these reagents, a portion of the anti-ligand will be combined with anti(anti-ligand)-$Ch_1$ and another portion with anti(anti-ligand)-$Ch_2$, so as to become bound. Desirably, the anti(anti-ligand) will be monofunctional, e.g. $F_{ab}$. The anti(anti-ligand)-$Ch_1$ and -$Ch_2$ bound to anti-ligand provides comparable reagent to receptor-$Ch_1$ and receptor-$Ch_2$ respectively. Similar ratios of anti(anti-ligand)-chromophores to anti-ligand may be employed as previously indicated.

In a preferred embodiment, anti-ligand from two different species, e.g. mammalian species, are employed, for example, sheep and cows. In this situation, the epitopic or haptenic sites are different for the two anti-ligands for the same ligand. In referring to anti-ligand from two different sources, anti-ligand will be preceded by a small letter, e.g. a-(anti-ligand). In this mode, the anti-ligand and anti(anti-ligand)-chromophore need not be precombined. The ratios of the various reagents would parallel the analogous reagents in the previously described assays.

The chromophore reagents would be anti(a-antiligand)-$Ch_1$ and anti(b-anti-ligand)-$Ch_2$. Thus, $Ch_1$ would be associated with only a-(anti-ligand) and $Ch_2$ with b-(anti-ligand).

This technique allows for the determination of assemblages in solution, where members of the assemblage differ by at least one epitopic site. One can prepare a-(anti-ligand) for one member of the assemblage and b-(anti-ligand) for another member of the assemblage. Quencher and fluorescer would be brought together only when the two members are bound together.

Using anti-ligand from two different sources can also be employed with advantage with a ligand to avoid having to precombine anti-ligand with the anti(antiligand)-chromophore and in situations where covalent linkage is occurring between two entities which can exist independently, e.g. undergoing a chemical reaction.

The reagents can be provided in separate vials or mixed in a dry lyophilized state or an aqueous, normally buffered (pH 5–10; usually 6.5–8.5) solution of any desired concentration. Preferably, anti(a-antiligand) would not be combined with a-(anti-ligand) in solution as a reagent for a long period prior to use. Conveniently, the two anti-ligands could be combined and the two anti(anti-ligand)s.

A particular advantage of using the double receptor is that the same pair of (anti(anti-ligand)-chromophore)s can be employed irrespective of the liqand, only the pairs of anti-ligand varying with the ligand.

For determining the presence of antibodies to a particular antigen, one would carry out the assay as if one was determining the antigen, except that a known amount of antigen would be added to the assay medium. Any antibody present in the unknown would act to diminish the amount of the anti(anti-ligand)-chromophore bound to the antigen and thus diminish the amount of quenching which would occur in the absence of antibody. Of course, the anti-ligand would be from different species (other than mammalian) than the antibody to be determined.

The following examples are offered by way of illustration and not by way of limitation.

EXPERIMENTAL (All temperatures not otherwise indicated are in Centigrade. All parts otherwise indicated are parts by weight. All buffer solutions are aqueous buffer. All symbols not otherwise defined are intended to have their normal meaning.)

The following symbols are employed:
IgG - gamma-globulin;
IgG(x) - anti-x;
R - tetramethylrhodamine, e.g. RIgG(x) tetramethylrhodamine conjugated to anti-x;
F - fluorescein, e.g. FIgG(x) fluorescein conjugated to anti-x; and
hIgG - human gamma-globulin.

EXAMPLE I

Fluorescein Isothiocyanate (FITC) Conjugate to $O^3$-aminoethylmorphine (FLUMO'S')

A. Fluorescein amine (0.5g) (Sigma, isomer I, pure, tlc MeOH/$CHCl_3$ 1:3) was dissolved in 20ml of dry acetone (dried on anh. $K_2CO_3$) and added dropwise at room temperature to 3ml of thiophosgene in 5ml of acetone with strong stirring (½ hr). Stirring was continued for 1 hour and the resulting precipitate, cooled with an ice-bath to 5°, was rapidly filtered through a fine sintered glass funnel. The precipitate was washed with dry acetone (3ml) and then with 5 × 5ml 6N HCl while crushing with a spatula until it all turned deep red, followed by drying in vacuo (80° KOH) overnight. The isothiocyanate obtained was pure (tlc 50% MeOH/DMF).

B. $O^3$-aminoethylmorphine (100mg) is dissolved in 5ml of acetone and added to a mixture of acetone (20ml), water (5ml), and triethylamine (0.07ml). To this solution is added a solution of FITC (100mg) in acetone (5ml) dropwise with stirring during 15 min. Stirring is continued for an additional 80 min, while adjusting the pH of the reaction mixture to 9.5 with drops of dilute triethylamine solution in acetone (1.4ml/10ml acetone). The acetone is then partially removed with a rotary evaporator at room temperature. The product is then precipitated by bubbling $CO_2$ through the solution with simultaneous addition of $H_2O$ (up to 10ml) until the pH drops to 6–6.5. The precipitate is rapidly filtered on a sintered glass funnel and washed with $H_2CO_3$ solution (2ml, pH 6.0). Yield 60mg. The filtrate and washings are combined and a second crop is obtained by repeating the bubbling of $CO_2$ as described. Yield 27mg. The product is dried overnight under vacuum at 80° over $P_2O_5$. Total 87mg. The product shows a single spot on tlc (50% methanol in dimethylformamide), Rf = 0.45.

EXAMPLE II

Purification and Labeling of Morphine Antibody (IgG(m)) with Tetramethylrhodamine Isothiocyanate (TRITC)

A. a. Preparation of Morphine - Immunoadsorbent

Cyanogen bromide activated Sepharose 4B coupled with hexamethylenediamine (8–10 μmole/1ml packed gel) was prepared according to the company's directions (Pharmacia, Upsala). Wet gel (2.5ml) was suspended in borate buffer (10ml, 0.1N, pH 8.8), the mixed anhydride of $O^3$-carboxymethylmorphine and isobutyl chloroformate (0.1 mmole, large excess) in DMF (2ml) added in the cold (0°), and the mixture allowed to react for 3 hours. The gel was filtered and washed sucessively with $H_2O$ (500ml), 0.1M borate buffer pH 9.0 (500ml), $H_2O$ (500ml), dilute HCl + 0.1M NaCl, pH 2.5 (1500ml), and $H_2O$ (1000 ml). No morphine could be detected at the end of the washings. The estimation of bound morphine was carried out be a dilute acetic acid hydrolyis method (Failla, et al., Anal. Biochem., 52, 363 (1973). The uv spectrum was compared to that of $O^3$-carboxymethylmorphine. The bound morphine equivalent was 5.05 μmole/1ml packed gel.

b. Purification of Morphine Antibody

The morphine Sepharose conjugate (2.5ml) was packed in a ¼ inch o.d. column and washed successively with 100ml each of borate buffer 0.1M pH 9.0, $H_2O$, dilute HCl pH 1.5, $H_2O$, and the same borate buffer. Stock sheep IgG solution (7ml, 2.18×10$^{-4}$M binding sites) was applied to the column followed by washing with borate buffer 0.1M pH 9.0, until no protein could be detected in the effluent (uv). All the antimorphine activity was retained by the column as determined by morphine spin-label measurement. (See U.S. Pat. No. 3,690,834). Washing was continued with glycine-HCl buffer 0.1N pH 4.0 whereby no protein was eluted. Antibody was then eluted with glycine-HCl buffer 0.1N pH 1.5 and 3ml fractions were collected at room temperature in tubes containing 1ml of 1N borate buffer pH 9.0. Almost all of the antibody was collected in three fractions which were combined and dialyzed for 24 hours against 0.1N phosphate buffer ph 7.5 (2×2000ml). The antimorphine activity of the isolated fraction was determined with morphine spin-label and accounted for 70% of the initially bound antimorphine activity. This fraction was 100% pure as determined by the antimorphine activity titer value compared to protein content estimated from the uv spectrum at 280nm.

B. a. Purification of Morphine Antibody-Sephadex Chromatography

The antimorphine IgG(m) solution (2ml, ~50mg/ml total protein) was separated on Sephadex G-200 column (2×30cm) with 0.01M PBS (phosphate buffered saline) pH 7.4 (flow rate 1ml/10min). The IgG clearly separated from the IgM and albumin and fractions of 2–3ml were collected. The obtained IgG showed no albumin on cellulose acetate electrophoresis (Tris-barb. buffer, pH 8.8, $\eta = 0.1$) and was 32–35% antimorphine-rich IgG. Recovery depended on the cut-width of the IgG peak collected and was usually 50% of total antimorphine activity applied to the column. The collected IgG fraction was dialyzed against 0.01M phosphate buffer pH 7.5.

b. Bovine Serum Albumin (BSA)-Immunoadsorbent Treatment

BSA was coupled with CNBr activated Sepharose 4B (Pharmacia) according to the company's instructions (50% excess of BSA was used over the recommended amount). Five ml of the Sephadex chromatographed IgG solution (20mg/ml) were applied to the BSA-immunoadsorbent column (1×15cm) and run through with 0.01M phosphate buffer pH 7.5. The collected protein came out in 20ml and was assayed for protein content (uv) and antimorphine activity (spin-label method). Recovery of protein was 70% and recovery of antimorphine activity was 90–92%.

c. Antimorphine (IgG(m)) Labeled with TRITC (RIgG(m))

To a solution of IgG(m) (7mg/0.5ml) in 0.01M phosphate buffer pH 7.5 is added crystalline potassium carbonate up to pH 10.0–10.5 with stirring at roon temperature. TRITC (tetramethylrhodamine isothiocyanate) (15–1000 μg) dissolved in acetone (3–30 μl) is then added and stirring is continued for 3 hrs. Initially the pH drops to 9.0 and then stays stable, and is maintained at 9.0–9.5 if necessary, by careful addition of crystalline potassium carbonate. The reaction mixture is then applied to a Sephadex G-25(M) column (1×15cm) with 0.01M phosphate buffer pH 7.5 and elution of the first colored band which separates completely from other bands is collected in 10–15 min. The separation is repeated twice in order to ensure complete removal of free dye. In case of formation of a precipitate, the precipitate is removed by centrifugation prior to the separation on Sephadex. The following table describes the preparation of conjugates with various degrees of labeling by the above procedure:

| Protein (% Antimorphine) | Concentration mg/0.5ml | Dye (TRITC) μg | D/P* μg | % Activity (M/M) | Recovery |
|---|---|---|---|---|---|
| IgG (45) | 7.1 | 15 | 0.9 | 86 | |
| IgG (45) | 7.1 | 50 | 2.2 | 89 | |
| IgG (45) | 7.1 | 150 | 4.4 | 75 | |
| IgG (45) | 7.1 | 400 | 15–16 | 75 | |
| IgG (45) | 7.1 | 750 | 20–23 | 70 | |

*D/P = Dye/Protein

EXAMPLE III

Fluorescein Isothiocyanate (FITC)-Labeled Morphine Antibody (FIgG(m))

a. Conjugation Procedure

Four 1ml fractions of affinity chromatographed morphine antibody (3.06mg protein/ml) (See Example II) in 0.01M phosphate buffer pH 7.5, were brought to pH 9.5 with crystalline sodium carbonate ($Na_2CO_3$). 10, 20, 30, and 50μl of an acetone solution of FITC (2mg/300μl) were added respectively to the four antibody fractions at room temperature with stirring. After 3 hrs, the four reaction mixtures were combined, then divided into 8 equal portions and each passed through Sephadex G-25 column (1×15cm) equilibrated with 0.01M phosphate buffer pH 7.5. Elution with the same buffer yielded (the first colored band) the conjugate which was free of unreacted dye.

b. Separation of FITC Conjugate on DEAE-Cellulose Column (See M. Goldman in "Fluorescent Antibody Methods," Academic Press ed., 1968, pp. 104–107). The FITC-antimorphine conjugate was applied to a DEAE-cellulose column (1×3cm) equilibrated with 0.01M phosphate buffer pH 7.3. Elution with the same buffer and with increasing NaCl concentration yielded fractions of increasing dye content. The dye content D/P of the various fractions was determined with the Wells' nomograph (A. F. Wells, C. E. Miller and M. K. Nadel, Appl. Microbiol, 14, 271 (1966). The antimorphine activity was determined as usual with morphine spin-label. The following fractions were obtained:

| Fraction No. | Protein mg | D/P mole/mole |
|---|---|---|
| 1 | 1.75 | 1.5 |
| 2 | 1.3 | 3.0 |
| 3 | 1.15 | 6.0 |
| 4 | 1.42 | 9.0 |

EXAMPLE IV

Purification of Antibody to Human Gamma-Globulin (IgG(hIgG)) and Conjugation with FITC (FIgG(hIgG)) and TRITC (RIgG(hIgG))

a. Purification of Antibody to Human IgG by Affinity Chromatography

Sepharose-4B (2g) was coupled with 18mg human gamma-globulin (hIgG) as described in the company manual (Pharmacia, Upsala). Rabit antiserum (50ml) to hIgG (5mg antibody/ml) (IgG(hIgG)) was obtained from Antibodies Incorporated. A column (1×3cm) of the above Sepaharose-hIgG conjugate was prepared with 0.01M borate buffer pH 8.0. The antiserum was passed through the column, followed by washing with the same buffer until no protein could be detected in the eluent. The column was further washed with 0.1M glycine.HCl buffer pH 5.0. The antibody was then eluted with 0.1M glycine.HCl buffer pH 2.5; fractions of 3ml were collected and immediately neutralized with 0.5M borate buffer 9.0. The total volume of antibody solution thus collected was 30ml. The antibody solution was dialyzed overnight against 0.05M phosphate buffer pH 8.0, then concentrated with Aquacide and dialyzed again. The final volume was 11ml and the protein-antibody content 3.76mg/ml as determined from the absorption spectrum at 280nm. Antibody recovered was 83%.

b. Preparation of FIgG(hIgG)

i. The above antibody solution (1ml) in 0.05M phosphate buffer pH 8.0 was brought to pH 9.5 with crystalline $Na_2CO_3$. FITC (100μg) in 10μl of acetone was added at room temperature and stirred for 3 hrs. The conjugate was then separated on Sephadex G-25(M) (1×10cm) equilibrated with 0.05M phosphate buffer pH 8.0. The conjugate was collected in 1.5ml; it had D/P = 4.3 (M/M) (dye/protein) and 2.05mg/ml as determined with the Wells' nomograph.

c. Preparation of RIgG(hIgG)

i. The above described antibody solution (1ml) in 0.05M phosphate buffer pH 8.0 was brought to pH 9.5 with crystalline $Na_2CO_3$. TRITC (0.5mg) in acetone (20–30μl) was added at room temperature and the mixture stirred for 3 hrs. A precipitate formed which was removed by centrifugation and discarded. The conjugate was then separated twice on Sephadex G-25 column (1×10cm) equilibrated with 0.05M phosphate buffer pH 8.0. The product was recovered in a 2ml volume and had D/P = 10 and 0.7mg/ml as determined from the absorption spectrum at 280 and 516nm.

ii. DEAE-cellulose separated IgG fraction (27.6mg/ml) of Rabbit antiserum to hIgG (6.4mg antibody/ml) was obtained from Antibodies Inc. The above protein solution (0.5ml) was brought to pH 9.5 with crystalline $Na_2CO_3$, and 3mg of TRITC in 50μl of acetone + 0.5ml $H_2O$ were added with stirring in the cold (4°). After 3 hrs. a precipitate occurred and was filtered off. The resulting violet solution was separated successively twice on Sephadex G-25(M) column (2×30cm) equilibrated with 0.05M phosphate buffer pH 8.0. The resulting conjugate was 0.1mg antibody/ml and had D/P = 12–15 (M/M) as calculated from the absorption spectrum.

EXAMPLE V

Conjugation of Human Gamma-Globulin (hIgG) to Fluorescein (FhIgG)

One mg of HIgG (Human IgG) dissolved in 0.4ml of 0.1M phosphate buffer pH 7.5, was brought to pH 9.5 with crystalline $Na_2CO_3$. A solution (10μl) of FITC (70μg) in acetone was added with stirring and mixed for 3 hrs at room temperature. The resulting solution was separated two times on Sephadex G-25(M) column (1×15cm) equilibrated with 0.05M phosphate buffer pH 8.0. The eluted FITC-hIgG conjugate solution was 0.58mg/ml in concentration and had D/P = 5.5 (M/M) as determined by the Wells' nomograph.

EXAMPLE VI

Morphine Conjugated to Bovine Serum Albumin (BSA-44m)

$O^3$-Carboxymethyl morphine (3.43g) and 1.31ml isobutyl chloroformate were combined in 30ml DMF at 0°. The resulting clear solution was then added to a stirring solution of 2.88g BSA and 13g $NaHCO_3$ in 600ml of water at 0°. Addition was carried out by means of a syringe with its tip below the solution surface. The solution was stirred in a cold room overnight.

After passing the solution through a large Sephadex column, the effluent was concentrated to 60ml with Dow HFD/1 overnight and lyophilized to yield 3.1g. By uv analysis the product was shown to have an average of about 44 morphine groups.

In order to demonstrate the effectiveness of the subject assays using quenching of fluorescence as a method of measuring the presence of a ligand, a number of different assays were carried out employing different protocols.

The first assay to be considered is the assay for morphine and codeine employing the fluorescein isothiocyanate conjugate to $O^3$-aminoethylmorphine (FLUMO'S').

As a first part of this assay, a number of antibody conjugates having varying degrees of labeling of rhodamine were combined with FLUMO'S' to determine the maximal quenching. The FLUMO'S' was at a concentration of $1.83×10^{-9}M$ in 0.05M borate buffer pH 8.0. Fluorescence relative intensity at $F_{max}$ = 516–518nm was recorded by scanning from 490nm to 530nm, excitation line was 462–464nm and slits were adjusted with sensitivity knob to keep the peak on scale with a Perkin-Elmer Model MPF-2A fluorescence spectrophotometer. The spectrophotometer cell, 1cm path length (3ml in volume), was installed in a two mirror combination-base. The conjugated antibody was allowed to incubate with FLUMO'S' at room temperature in pyrex vials for 30–40 min before taking the fluorescence reading.

The dye/protein ratio (D/P) (M/M) for the conjugates was 0.9, 2.2, 4.4, 15–16, and 20-22. The results reported for relative efficiency (1/2 of the maximum quenching in % divided by the corresponding number of binding site equivalents) were respectively 6, 16.4, 24, 51.4, and 31.5.

In carrying out the assay, the following reagents were employed: FLUMO'S' - $1.38×10^{-7}M$; RIgG(m) D/P 30, $4.58×10^{-7}M$; borate buffer 0.05M pH 8.0; standard morphine solutions ($1.5×10^{-3}$–$1.5×10^{-7}M$). Incubation was in glass tubes.

Procedure: equal amounts of RIgG(m) (40μl) were diluted with 0.05M borate buffer, pH 8.0 (2940-2990μl) and incubated at room temperature with increasing amounts of morphine (5-10μl of the standard morphine solutions) for one hour. FLUMO'S' (10μl) was then added and the mixture incubated for an additional 1 hour. The final volume of each tube was 3ml. The final concentration of FLUMO'S' was $4.6\times10^{-10}$M and that of RIgG(m) $6.1\times10^{-9}$M in binding sites. The results are reported in the following table as fluorescence intensity increase as percent of maximum fluorescence possible (FLUMO'S' without quenching antibody).

TABLE I

| morphine (molarity) | signal intensity | % of $F_{max}$ |
|---|---|---|
| 0 | 27 | 33.33 |
| $2.5\times10^{-9}$ | 28 | 34.5 |
| $5\times10^{-9}$ | 29.5 | 36.4 |
| $2.5\times10^{116\,H}$ | 35 | 43.2 |
| $5\times10^{-8}$ | 38 | 46.9 |
| $2.5\times10^{-7}$ | 54 | 66.6 |
| $5\times10^{-7}$ | 60 | 74 |
| $2.5\times10^{-6}$ | 74 | 91.3 |
| $5\times10^{-6}$ | 78 | 96.3 |

The study was repeated except that codeine was employed in place of morphine. The following table indicates the results.

TABLE II

| Codeine (molarity) | signal intensity | % of $F_{max}$ |
|---|---|---|
| 0 | 27 | 32.9 |
| $2.5\times10^{-9}$ | 30.5 | 37.2 |
| $5\times10^{-9}$ | 36 | 43.9 |
| $2.5\times10^{-8}$ | 51 | 62.2 |
| $5\times10^{-8}$ | 58 | 70.7 |
| $5\times10^{-7}$ | 75 | 91.5 |
| $2.5\times10^{-6}$ | 80 | 97.5 |

The assay was repeated, but instead of the rhodamine labeled morphine antibody (RIgG(m)) having a D/P (dye/protein) (M/M) ratio of 30, RIgG(m) was employed having a D/P of 22. The following are the results employing morphine.

TABLE III

| morphine (molarity) | signal intensity | % of $F_{max}$ |
|---|---|---|
| 0 | 24.5 | 29.9 |
| $2.5\times10^{-10}$ | 26.0 | 31.7 |
| $5\times10^{-10}$ | 26.5 | 32.3 |
| $2.5\times10^{-9}$ | 28.0 | 34.1 |
| $5\times10^{-9}$ | 29.0 | 35.4 |
| $1\times10^{-8}$ | 33.5 | 40.8 |
| $2.5\times10^{-8}$ | 40.0 | 48.8 |
| $5\times10^{-8}$ | 45.5 | 55.5 |
| $1\times10^{-7}$ | 53.0 | 64.6 |
| $2.5\times10^{-7}$ | 63.0 | 76.8 |
| $5\times10^{-7}$ | 68.0 | 82.9 |
| $1\times10^{-6}$ | 72.5 | 88.4 |
| $2.5\times10^{-6}$ | 80.0 | 97.5 |
| $5\times10^{-6}$ | 82.0 | 100 |

The next study which was carried out employed a polyligand, namely, morphine conjugated to bovine serum albumin, having an average number of 44 morphines per albumin. In a first test, the polyligand was employed as a synthetic protein in that the polyligand has a plurality of morphine epitopic sites. In a second series of tests, the polyligand was employed in an assay for morphine or codeine. In both these assays, neither chromophore is covalently bound to the epitopic site of interest, but rather each becomes bound through antibody. Thus, there is a random binding of antibody to morphine on the polyligand. At the concentrations of interest, in a study not described here, it was found that optimum quenching was obtained where a ratio of quencher as receptor-quencher to fluorescer as receptor-fluorescer was about 5 to 1.

In the first test, which is an assay for the poly(ligand analog), a series of tubes were prepared each containing $6.4\times10^{-9}$M (in binding sites) of antimorphine having a D/P ratio of fluorescein/antibody of 9 and $3.47\times10^{-8}$M (in binding sites) of antimorphine having a D/P ratio of rhodamine/antibody of about 22 in 0.05M phosphate buffer, pH 8.0, containing $1.2\times10^{-6}$M bovine gamma-globulin. Various amounts of the morphine conjugated bovine serum albumin (approximately 44 morphines per albumin) (0.012-1.2μg) were added (in 5-10μl) to each of the tubes so that the final volume was 0.5ml and incubated at room temperature for 30 min. The fluorescence of each of the tubes is then measured and expressed in percentage of maximal fluorescence possible (when no morphine conjugated BSA is present). The results are in the following table.

TABLE IV

| 44m-BSA μg (added) | % of $F_{max}$ |
|---|---|
| 0 | 100 |
| 0.012 | 84.5 |
| 0.024 | 72 |
| 0.048 | 64.5 |
| 0.084 | 61 |
| 0.12 | 66 |
| 0.24 | 74 |
| 0.48 | 83 |
| 1.20 | 92 |

For assaying for codeine, the following procedure was employed. Employing the same antimorphine-fluorescein (FIgG(m)) and antimorphine-rhodamine (RIgG(m)) as employed above, 30μl of the FIgG(m) ($2.64\times10^{-7}$M) and 30μl of the RIgG(m) ($1.44\times10^{-6}$M) were diluted in a series of tubes with 0.05M phosphate buffer, pH 8.0, containing $1.5\times10^{-6}$M bovine gamma-globulin (390-430μl) Codeine in increasing concentrations ($1.5\times10^{-3}$–$1.5\times\lambda$ $10^{-6}$M) is then added (10-14μl) and the mixture incubated at room temperature for 0.5 hr. To each of the tubes is then added 10μl (0.24μg) of the morphine-bovine serum albumin conjugate used previously and the tubes incubated for an additional one hour. The final volume in each tube was 0.5ml. The fluorescence of each of the tubes at 518nm was then recorded and expressed as percentage of maximal fluorescence possible (when no morphine-BSA conjugate is present). The following table indicates the results.

TABLE V

| Codeine (M) | % of $F_{max}$ |
|---|---|
| 0 | 49 |
| $3\times10^{-9}$ | 51 |
| $6\times10^{-9}$ | 54 |
| $1.2\times10^{-8}$ | 56.5 |
| $3\times10^{-8}$ | 62 |
| $6\times10^{-8}$ | 70.5 |
| $1.2\times10^{-7}$ | 81 |
| $3\times10^{-7}$ | 90.5 |
| $6\times10^{-7}$ | 94.5 |
| $1.2\times10^{-6}$ | 100 |

TABLE V-continued

| Codeine (M) | % of $F_{max}$ |
|---|---|
| $3 \times 10^{-6}$ | 100 |

The next two studies involve the natural protein human gamma-globulin. In the first study, human gamma-globulin-fluorescein (FhIgG) D/P 5.5 was employed for the determination of human gamma-globulin. A series of tubes were prepared, each containing 100μl of 0.017mg/ml of anti-human gamma-globulin-rhodamine conjugate (RIgG(hIgG) D/P 12–15 in 0.05M phosphate buffer, pH 8.0 (330–380μl) containing BSA (0.6mg/ml). Increasing amounts of human gamma-globulin (in 15–35μl) were then added and incubated for 30 min at room temperature. To the solutions was then added 30μl of 0.014mg/ml of FhIgG. The final volume in each case was 0.5ml. The final concentration of the FhIgG was $5.4 \times 10^{-9}$M, while the concentrations of human gamma-globulin ranged from $4.84 \times 10^{-10}$ to $6.45 \times 10^{-8}$M. After a second incubation period of 30 min, the fluorescence of the tubes at 522nm was recorded as percentage of maximal fluorescence possible. The following table indicates the results.

TABLE VI

| HIgG (M) | % of $F_{max}$ |
|---|---|
| 0 | 28 |
| $4.84 \times 10^{-10}$ | 33 |
| $8.06 \times 10^{-10}$ | 36 |
| $1.13 \times 10^{-9}$ | 38 |
| $1.61 \times 10^{-9}$ | 46 |
| $3.22 \times 10^{-9}$ | 68 |
| $4.84 \times 10^{-9}$ | 81 |
| $8.06 \times 10^{-9}$ | 91 |
| $1.13 \times 10^{-8}$ | 93 |
| $1.61 \times 10^{-8}$ | 95.5 |
| $3.22 \times 10^{-8}$ | 96 |
| $6.45 \times 10^{-8}$ | 98 |

In the next determination, the human gamma-globulin was assayed by employing anti-human gamma-globulin-fluorescein (FIgG(hIgG)) conjugate and anti-human gamma-globulin-rhodamine conjugate (RIgG-(hIgG)). The fluorescein conjugate had a D/P of 4.3 and the rhodamine conjugate had a D/P of 10. All reagents were diluted with 0.05M phosphate buffer, pH 8.0, containing 0.6mg/ml of bovine serum albumin. A series of tubes were prepared, each containing 400μl of the indicated buffer. To each of the tubes was added, 30μl of 2.7μg/ml of FIgG(hIgG) and 30μl of 35μg/ml of RIgG(hIgG). The tubes were mixed and increasing amounts of human gamma-globulin added in 40μl solutions and incubated at room temperature for 1 hour. Th fluorescence of the tubes was then measured and expressed as percent of total fluorescence in the absence of human gamma-globulin. The following table indicates the results.

TABLE VII

| Human IgG(M) | % of $F_{max}$ |
|---|---|
| $3 \times 10^{-11}$ | 100 |
| $6 \times 10^{-11}$ | 95.7 |
| $1.2 \times 10^{-10}$ | 93.2 |
| $1.8 \times 10^{-10}$ | 89.5 |
| $2.4 \times 10^{-10}$ | 86.5 |
| $3 \times 10^{-10}$ | 82.2 |
| $6 \times 10^{-10}$ | 70.5 |
| $1.2 \times 10^{-9}$ | 60.7 |
| $1.8 \times 10^{-9}$ | 62 |
| $2.4 \times 10^{-9}$ | 68.1 |
| $3 \times 10^{-9}$ | 69.3 |
| $6 \times 10^{-9}$ | 79 |
| $1.2 \times 10^{-8}$ | 87.7 |
| $1.8 \times 10^{-8}$ | 88.3 |
| $2.4 \times 10^{-8}$ | 93.8 |

As is evidenced from the above Table VII, with increasing human gamma-globulin concentration, the fluorescence decreases to a minumum and then increases. Therefore, with an unknown, it would be necessary to carry out two dilutions to determine which part of the curve was involved.

The above results demonstrate the extreme sensitivity and wide range of capability of the subject assays. By employing the fluorescence-quenching phenomenon, one can assay directly for a wide variety of different compounds, both haptenic an antigenic. Reagents can be employed, where the hapten or antigen is covalently bonded to the chromophore, or alternatively, where the compound of interest has a plurality of epitopic sites, mixtures of antibodies can be employed with a portion of the antibodies bonded to quencher and a portion of the antibodies bonded to fluorescer. In this situation, derivatives of the ligand are not required for preparing reagents, where a naturally occurring receptor is available or the ligand is antigenic.

In addition, reagents can be prepared having a plurality of haptenic or antigenic molecules bonded to a nucleus molecule. Either the nucleus molecule can be bonded to a chromophore and antibody employed which is conjugated to the other member of the fluorescer-quencher pair or the mixture of antibodies indicated above employed. The assay is relatively rapid, and depending upon the concentrations, various incubation times are required. Furthermore, conventional fluorometers can be employed which are relatively inexpensive and easily read.

Although the foregoing invention has been described in some detail by way of illustration and example for purposes of clarity of understanding, it will be obvious that certain changes and modifications may be practiced within the scope of the appended claims.

What is claimed is:

1. A method for determining in an assay solution, the presence of a ligand in an unknown suspected of containing said ligand, said ligand having at least one epitopic site, wherein two chromophores, $Ch_1$ and $Ch_2$, which form a fluorescer-quencher pair are employed as reagents, whereby in said assay solution the amount of fluorescer brought within quenching distance of said quencher is affected by the presence of ligand, which comprises:

A. combining in an aqueous buffered medium to form an assay solution;
1. said unknown;
2. a source of $Ch_1$, as $Ch_1$ covalently bound to a first receptor composition capable of specific non-covalent binding to said ligand;
3. a source of $Ch_2$, as $Ch_2$ covalently bound to a second receptor composition capable of specific non-covalent binding to said ligand or as $Ch_2$ covalently or non-covalently bound to ligand analog, wherein ligand analog is a mono- or polyvalent radical, a substantial proportion of which defines one or more epitopic sites capable of competing with ligand for the binding sites of said receptor;

B. incubating said assay solution for a sufficient time for at least a portion of said receptor compositions to combine with at least a portion of any ligand present;

C. irradiating said incubated assay solution with light at a wavelength within the absorption spectrum of said fluorescer; and D. measuring the amount of fluorescence from said assay solution as compared to an assay solution having a known amount of ligand.

2. A method according to claim 1, wherein said first and second receptor compositions are the same anti-ligand.

3. A method according to claim 1, wherein said first receptor composition is a combination of anti-ligand from a first species and anti(first anti-ligand) conjugated to $Ch_1$, and said second receptor composition is anti-ligand from a second species and anti(second anti-ligand) conjugated to $Ch_2$.

4. A method according to claim 1, wherein said ligand is of from about 110–2,000 molecular weight.

5. A method according to claim 1, wherein said ligand is a poly(amino acid) having a plurality of epitopic sites and of at least about 10,000 molecular weight.

6. A method according to claim 1, wherein said ligand is of greater than about 2,000 molecular weight and has a plurality of epitopic sites, and said sources of $Ch_1$ and $Ch_2$ are said first and second receptor compositions covalently bonded to $Ch_1$ and $Ch_2$ respectively.

7. A method according to claim 6, wherein said ligand is a serum protein.

8. A method according to claim 7, wherein said serum protein is a globulin.

9. A method according to claim 7, wherein said serum protein is an albumin.

10. A method according to claim 7, wherein said serum protein is a lipoprotein.

11. A method according to claim 7, wherein said serum protein is a glycoprotein.

12. A method according to claim 7, wherein said serum protein is a complement factor.

13. A method according to claim 7, wherein said serum protein is a blood clotting factor.

14. A method according to claim 6, wherein said ligand is at least a portion of a microorganism.

15. A method according to claim 14, wherein said ligand is a portion of the microorganism membrane.

16. A method according to claim 14, wherein said microorganism is a virus.

17. A method according to claim 6, wherein said ligand is a poly(amino acid) of greater than about 10,000 molecular weight.

18. A method according to claim 1, wherein said ligand is an assemblage of an antigen and antibody for said antigen.

19. A method according to claim 1, wherein said receptor compositions are antibodies, said aqueous medium has from 0 to 20 volume percent of an inert polar organic solvent, said aqueous medium is buffered in the range of from about 5 to 10, the amount of receptor added is sufficient to provide from about 20 to 80 percent quenching and the assay solution is incubated at a temperature in the range of about 0° to 45° C.

20. A method for determining in an assay solution, the presence of a ligand in an unknown suspected of containing said ligand, said ligand having one or more epitopic sites;

in which is employed two chromophores, $Ch_1$ and $Ch_2$, which form a fluorescer-quencher pair, one of the chromophores, $Ch_1$, is bound to receptor for ligand to form receptor-$Ch_1$, said receptor having binding sites capable of specifically binding to the epitopic sites of said ligand, the other of the chromophores, $Ch_2$, is bound to receptor for ligand to form receptor-$Ch_2$ or to ligand analog, either a single ligand analog being covalently bound to one or more chromophores to form ligand analog-$(Ch_2)_x$, where $x$ is on the average at least one, or a plurality of ligand analogs and chromophores being covalently bound to a polyfunctionalized nucleus molecule to form poly(ligand analog)-poly($Ch_2$), wherein ligand analog is a mono- or polyvalent radical, a substantial proportion of which defines one or more epitopic sites capable of competing with ligand for the binding sites of said receptor; and wherein the amount of fluorescer within quenching distance of quencher is related to the amount of ligand present in said assay solution;

which comprises:

A. combining in an aqueous buffered medium to form an assay solution:
1. unknown;
2. receptor-$Ch_1$; and
3. a source of $Ch_2$ capable of binding within quenching distance to receptor-$Ch_2$, as one of the following:
    a. ligand analog-$(Ch_2)_x$;
    b. poly(ligand analog)-poly($Ch_2$);
    c. poly(ligand analog) and receptor-$Ch_2$;

wherein poly(ligand analog) has a plurality of ligand analogs covalently bound to a polyfunctionalized nucleus molecule; or when said ligand has a plurality of epitopic sites,
    d. receptor-$Ch_2$;

B. incubating said assay solution for a sufficient time for at least a portion of the receptor present to combine with at least a portion of any ligand present;

C. irradiating said incubated assay solution with light at a wavelength within the absorption spectrum of said fluorescer; and D. measuring the amount of fluorescence from said assay solution as compared to an assay solution having a known amount of ligand.

21. A method according to claim 20, wherein said ligand is of from about 110 to 2,000 molecular weight, and said receptor is antibody.

22. A method according to claim 20, wherein said ligand is a poly(amino acid) having a plurality of epitopic sites and of at least about 10,000 molecular weight.

23. A method according to claim 20, wherein said ligand is of greater than about 2,000 molecular weight and has a plurality of epitopic sites, said receptor is antibody, and said source of $Ch_2$ is receptor-$Ch_2$.

24. A method for determining in an assay solution, the presence of a ligand in an unknown suspected of containing said ligand, said ligand having one epitopic site, in which is employed two chromophores, $Ch_1$ and $Ch_2$, which form a fluorescer-quencher pair, one of the chromophores, $Ch_2$ is bound to receptor for ligand to form receptor-$Ch_1$, said receptor having a binding site capable of specifically binding to the epitopic site of said ligand, the other of the chromophores is covalently bound to ligand analog to form ligand analog-$Ch_2$, wherein ligand analog is a monovalent radical, a substantial proportion of which defines an epitopic site capable of competing with ligand for a binding site of said receptor; and wherein the amount of fluorescer within quenching distance of quencher is related to the amount of ligand present in said assay solution;

which comprises:
 A. combining in an aqueous buffered medium at a pH in the range of about 5 to 10 to form an assay solution;
  1. unknown;
  2. receptor-$Ch_1$;
  3. ligand analog-$Ch_2$;
 the concentrations of receptor-$Ch_1$ and ligand analog-$Ch_2$ providing from about 20 to 80% quenching of the fluorescence in the absence of ligand;
 B. incubating said assay solution at a temperature in the range of about 0–45° C for a sufficient time for at least a portion of the receptor present to combine with at least a portion of any ligand present;
 C. irradiating said incubated assay solution with light at a wavelength within the absorption spectrum of said fluorescer; and
 D. measuring the amount of fluorescence from said assay solution as compared to an assay solution having a known amount of ligand.

25. A method according to claim 24, wherein said ligand is of from about 110 to 2,000 molecular weight and is a drug having a benzene ring separated from an amino group by from 2 to 3 aliphatic carbon atoms.

26. A method according to claim 24, wherein said ligand is a steroid.

27. A method for determining in an assay solution, the presence of a ligand in an unknown suspected of containing said ligand, said ligand having a plurality of epitopic sites,
 in which is employed two chromophores, $Ch_1$ and $Ch_2$, which form a fluorescer-quencher pair, one of the chromophores, $Ch_1$, is bound to receptor for ligand to form receptor-$Ch_1$, said receptor having binding sites capable of specifically binding to the epitopic sites of said ligand, the other of the chromophores is bound to receptor for ligand to form receptor-$Ch_2$;
 wherein the amount of fluorescer within quenching distance of quencher is related to the amount of ligand present in said assay solution;
 which comprises:
  A. combining in an aqueous buffered medium at a pH in the range of about 5 to 10, to form an assay solution;
   1. unknown;
   2. receptor-$Ch_1$;
   3. receptor-$Ch_2$;
  B. incubating said assay solution at a temperature in the range of about 0°–45° C for a sufficient time for at least a portion of the receptor present to combine with at least a portion of any ligand present;
  C. irradiating said incubated assay solution with light at a wavelength within the absorption spectrum of said fluorescer; and
  D. measuring the amount of fluorescence from said assay solution as compared to an assay solution having a known amount of ligand.

28. A method according to claim 27, wherein said ligand is a poly(amino acid) of at least about 10,000 molecular weight.

29. A method for determining in an assay solution, the presence of a ligand in an unknown suspected of containing said ligand, said ligand having one or more epitopic sites,
 in which is employed two chromophores, $Ch_1$ and $Ch_2$, which form a fluorescer-quencher pair, one of the chromophores, $Ch_1$, is bound to receptor for ligand to form receptor-$Ch_1$, said receptor having binding sites capable of specifically binding to the epitopic sites of said ligand, the other of the chromophores is bound to receptor for ligand to form receptor-$Ch_2$;
 wherein the amount of fluorescer within quenching distance of quencher is related to the amount of ligand present in said assay solution;
 which comprises:
  A. combining in an aqueous buffered medium at a pH in the range of 5 to 10 to form an assay solution;
   1. unknown;
   2. receptor-$Ch_1$;
   3. poly(ligand analog) and receptor-$Ch_2$, wherein ligand analog is a mono- or polyvalent radical, a substantial proportion of which defines one or more epitopic sites capable of competing with ligand for the binding sites of said receptor and poly(ligand analog) has a plurality of ligand analogs covalently bound to a polyfunctionalized nucleus molecule;
  B. incubating said assay solution at a temperature in the range of about 0–45° C for a sufficient time for at least a portion of the receptor present to combine with at least a portion of any ligand present;
  C. irradiating said incubated assay solution with light at a wavelength within the absorption spectrum of said fluorescer; and
  D. measuring the amount of fluorescence from said assay solution as compared to an assay solution having a known amount of ligand.

30. A method according to claim 29, wherein said ligand has one epitopic site and is of a molecular weight in the range of about 110 to 2,000.

31. A method according to claim 30, wherein said ligand is a drug having a benzene ring separated by from 2 to 3 aliphatic carbon atoms from an amino group.

32. A method according to claim 30, wherein said ligand is a steroid.

33. A method according to claim 29, wherein said polyfunctionalized nucleus molecule is a poly(amino acid) of at least 30,000 molecular weight.

34. A method for determining in an assay solution the presence of a ligand or anti-ligand in an unknown suspected of containing said ligand or anti-ligand, said ligand and anti-ligand having a plurality of epitopic sites;
 in which is employed anti(anti-ligand), a portion of which is bound to $Ch_1$ and a portion of which is bound to $Ch_2$, wherein $Ch_1$ and $Ch_2$ form a fluorescer-quencher pair;

combining with said unknown (1) anti-ligand for the determination of the presence of ligand, or (2) ligand for the determination of the presence of anti-ligand;

separating anti-ligand bound to ligand from unbound anti-ligand;

combining in an aqueous buffered assay solution said bound anti-ligand with said anti(anti-ligand)s;

irradiating said assay solution with light at a wavelength within the absorption spectrum of said fluorescer; and measuring the amount of fluorescence from said assay solution as compared to an assay solution having a known amount of ligand or anti-ligand.

35. A method for determining in an assay solution the presence of a ligand in an unknown suspected of containing said ligand, said ligand having a plurality of epitopic sites, in which method is employed a-(anti-ligand), b-(anti-ligand), anti(a-(anti-ligand)-$Ch_1$ and anti(b-(anti-ligand)-$Ch_2$, wherein $a$ and $b$ designate a different species source for the anti-ligand and $Ch_1$ and $Ch_2$ form a fluorescer-quencher pair, wherein the amount of fluorescer within quenching distance of quencher is related to the amount of ligand present in said assay solution, which comprises:
A. combining in an aqueous buffered medium to form an assay solution:
1. unknown;
2. a-(anti-ligand);
3. b-(anti-ligand);
4. anti(a-(anti-ligand)-$Ch_1$; and
5. anti(b-(anti-ligand)-$Ch_2$;
B. incubating said assay solution for a sufficient time for at least a portion of the anti-ligands and anti)anti-ligand)s to combine with ligand and anti-ligand respectively;
C. irradiating said incubated assay solution with light at a wavelength within the absorption spectrum of said fluorescer; and
D. measuring the amount of fluorescence from said assay solution as compared to an assay solution having a known amount of ligand.

36. A method for determining in an assay solution, the presence of anti-ligand for a ligand in an unknown suspected of containing said anti-ligand, in said method is employed (anti-ligand)-$Ch_1$ and (anti-ligand)-$Ch_2$, wherein $Ch_1$ and $Ch_2$ form a fluorescer-quencher pair;

wherein anti-ligand present in the unknown diminishes the amount of quenching of said fluorescer by said quencher; and which comprises:
combining in an aqueous buffered assay medium:
1. said unknown;
2. said ligand, when said ligand is polyepitopic, or poly(ligand analog) when said ligand is monoepitopic;
3. (anti-ligand)-$Ch_1$; and
4. (anti-ligand)-$Ch_2$;

irradiating said assay solution with light at a wavelength within the absorption spectrum of said fluorescer; and measuring the amount of fluorescence from said assay solution as compared to an assay solution having a known amount of anti-ligand.

37. In combination, anti(a-anti-ligand)-$Ch_1$ and anti(b-anti-ligand)-$Ch_2$ wherein a and b designate antiligand from two different species for the same ligand, said ligand having a plurality of epitopic sites, and $Ch_1$ and $Ch_2$ designate a fluorescer-quencher pair.

38. A combination according to claim 37, including a-(anti-ligand) and b-(anti-ligand).

* * * * *